(12) United States Patent
Hanada et al.

(10) Patent No.: US 6,206,909 B1
(45) Date of Patent: Mar. 27, 2001

(54) PORTABLE WARMER SUITABLE FOR A BODY

(75) Inventors: Touru Hanada, Takarazuka; Kiyonobu Yoshida, Ikoma; Kouji Nakai, Wakayama; Shigehiro Kimura, Ikoma; Hidetaka Yabuuchi, Takarazuka; Takaaki Kusaka, Akashi, all of (JP)

(73) Assignee: Matsushita Electric Industrial Col Ltd., Osaka (JP)

( * ) Notice: Subject to any disclaimer, the term of this patent is extended or adjusted under 35 U.S.C. 154(b) by 0 days.

(21) Appl. No.: 09/052,007

(22) Filed: Mar. 31, 1998

(30) Foreign Application Priority Data

| | | |
|---|---|---|
| Mar. 31, 1997 | (JP) | 9-079468 |
| Dec. 11, 1997 | (JP) | 9-341128 |
| Mar. 4, 1998 | (JP) | 10-051729 |

(51) Int. Cl.⁷ .................................................. A61F 7/00
(52) U.S. Cl. .................................... 607/108; 607/112
(58) Field of Search .................... 607/108, 112, 607/149, 152; 2/44; 219/211, 527

(56) References Cited

U.S. PATENT DOCUMENTS

| | | | |
|---|---|---|---|
| 912,527 | * | 2/1909 | Batter . |
| 4,180,922 | * | 1/1980 | Cieslak et al. ............................ 36/2.6 |
| 4,281,418 | * | 8/1981 | Cieslak et al. ............................ 2/160 |
| 4,685,442 | * | 8/1987 | Cieslak ................................... 126/204 |
| 5,665,057 | * | 9/1997 | Murphy ..................................... 602/19 |
| 5,928,275 | * | 7/1999 | Yates et al. ............................. 607/112 |

FOREIGN PATENT DOCUMENTS

| | | |
|---|---|---|
| 2851602 | 6/1980 | (DE) . |
| 0014300 | 8/1980 | (EP) . |
| 2708196 | 2/1995 | (FR) . |
| 48-60708 | 8/1973 | (JP) . |
| 49-108290 | 9/1974 | (JP) . |
| 50-8039 | 3/1975 | (JP) . |

* cited by examiner

*Primary Examiner*—Linda C. M. Dvorak
*Assistant Examiner*—Jocelyn Debra Ram
(74) *Attorney, Agent, or Firm*—Israel Gopstein

(57) ABSTRACT

A fuel tank stores fuel gas. A catalytic burning section is connected to the fuel tank for generating heat based on an oxidative reaction between the fuel supplied from the fuel tank and air. The fuel tank and the catalytic burning section are assembled as a catalytic heat generating apparatus. The catalytic heat generating apparatus is detachably installed in a housing of a heater section. The heater section has both ends provided with a pair of belt portions wound around a user's body.

22 Claims, 5 Drawing Sheets

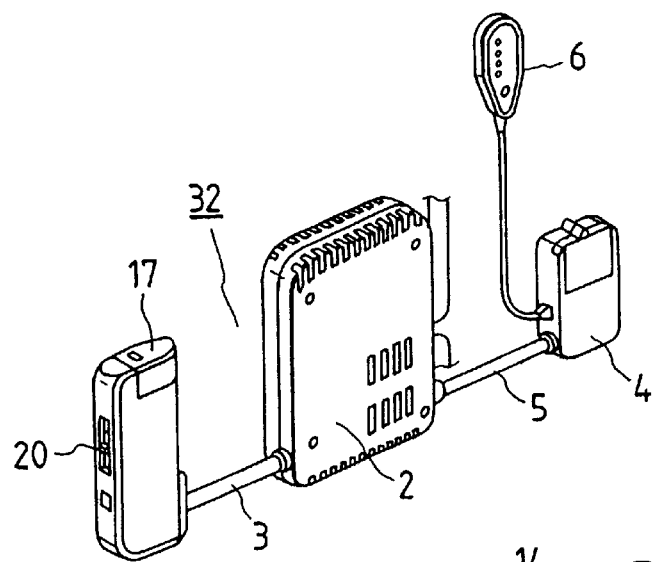
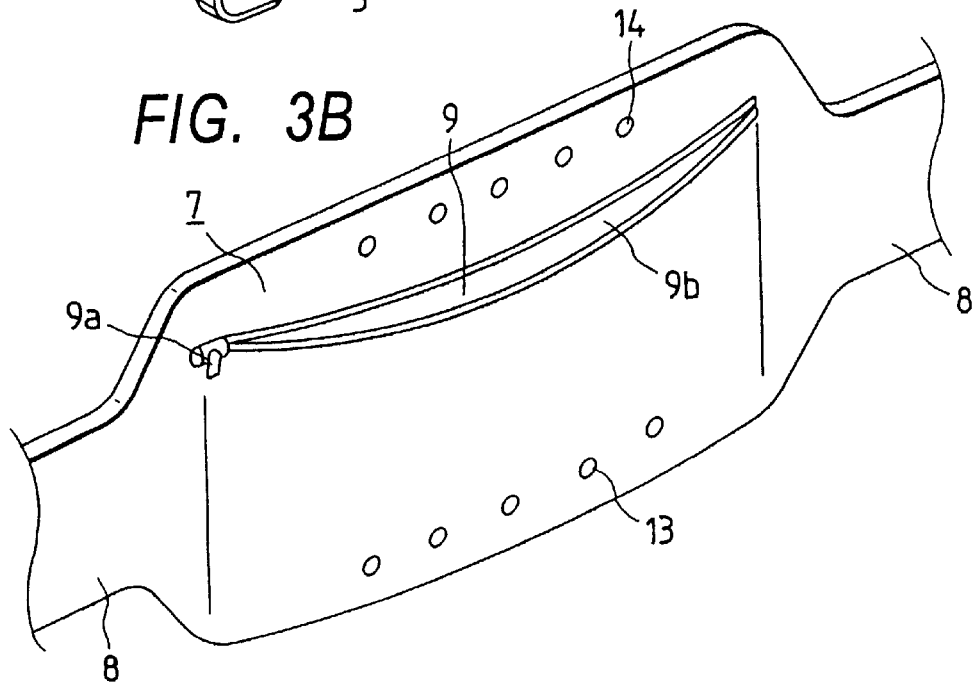

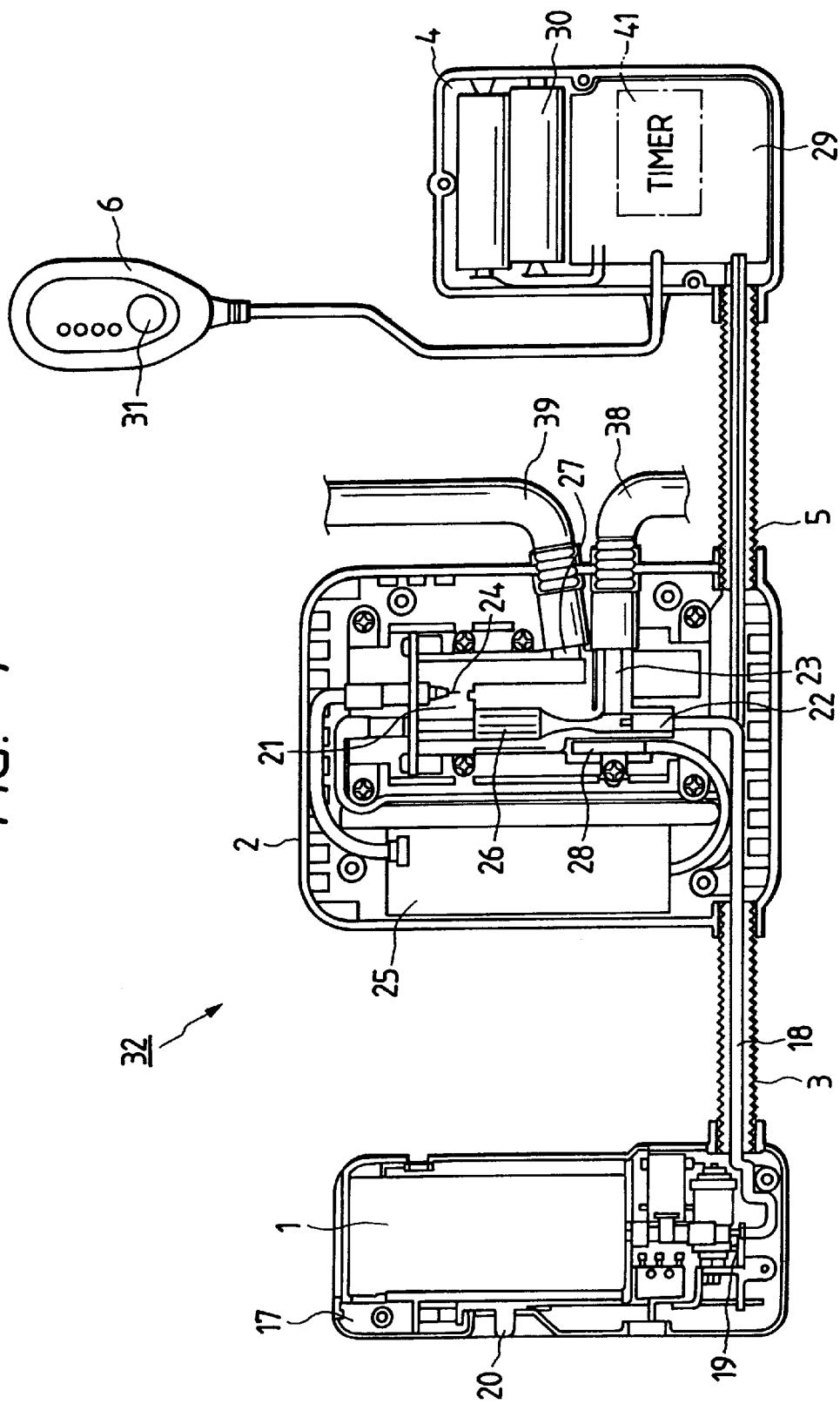

PORTABLE WARMER SUITABLE FOR A BODY

BACKGROUND OF THE INVENTION

The present invention relates to a portable warmer suitable for a user's body that utilizes heat generated from an oxidative reaction between liquefied petroleum gas and air.

As a conventional warmer, Unexamined Japanese Utility Model Application No. 49-108290, published in 1974, discloses an electric heating belt accommodating an electric heater with a battery supplying electric power to the electric heater.

According to this conventional warmer, there is a shortage of heat energy produced from the electric heater due to a limited capacity of the battery. Increasing a battery power may be possible, however it will result in undesirable increases in battery size and weight. Therefore, it is not practical to use this conventional warmer as a warming device for a human body.

To obtain a sufficient amount of electric power, it will be possible to connect the warmer to a commercial power source via an electric cord instead of using the battery. However, this cannot realize a portable warmer.

Unexamined Japanese Utility Model Application No. 48-60708, published in 1973, discloses a jacket accommodating a platinum catalytic burning apparatus.

According to this conventional warmer, the heavy burning apparatus will fairly increase the weight of the jacket. This will be uncomfortable for a user. The burning apparatus needs to be removed from the jacket every time the jacket is washed. It is not convenient.

Furthermore, Japanese Utility Model No. 50-8039, published in 1975, discloses a foot warmer that utilizes a catalytic combustion of liquefied petroleum gas.

Moreover, conventional pocket heaters are generally known as utilizing a chemical reaction of iron oxide powders and having an adhesive member for fixing a heater body to an arbitrary portion.

The conventional warmer utilizing a chemical reaction is inherently disadvantageous in that the temperature cannot be controlled, it cannot be used for a long time, and it is basically a disposable type.

SUMMARY OF THE INVENTION

In view of the foregoing, a principal object of the present invention is to provide a warmer capable of warming a user's body safely, satisfactorily and accurately.

In order to accomplish the above and other related objects, the present invention provides a warmer comprising a catalytic heat generating apparatus comprising a fuel tank for storing fuel gas and a catalytic burning section connected to the fuel tank. The catalytic burning section generates heat based on an oxidative reaction between the fuel supplied from the fuel tank and air. The catalytic heat generating apparatus is accommodated in a housing of a heater section. The heater section having both ends connected to a pair of belt portions which are to be wound around the user's body when the warmer is used for fixing the heater section to an intended portion of the user's body.

Preferably, the housing has an opening for taking the catalytic heat generating apparatus into and out of the housing. The catalytic burning section may be securely held in the housing by a fixing member.

The catalytic heat generating apparatus may comprise a plurality of separate units, and the fuel tank is connected to the catalytic burning section via a flexible connecting member.

Preferably, the heater section comprises a plurality of ventilation holes for communicating an inside space of the housing with an external space. In this case, at least part of the ventilation holes is provided on a bottom of the housing.

The catalytic burning section may comprise an intake section for introducing air from the external space and an exhaust section for emitting combustion gas. At least one passage is provided to connect either of the intake and exhaust sections to the external space. In this case, one end of the passage is connected to either of the intake and exhaust sections while the other end is extended to one of the belt portions and communicated with the external space.

Furthermore, the heater section may comprise a heat transfer board for diffusing the heat generated from the catalytic burning section.

Preferably, a cushion member is provided on at least one of the heater section and the belt portions.

The fuel tank may be detachable from the catalytic heat generating apparatus, and a storage is provided on at least one of the belt sections for storing a spare fuel tank.

It is further preferable that the warmer of the present invention comprises a control section for feedback controlling a temperature of the catalytic burning section to a set value. The control section may be associated with a handy controller for allowing a user to set a desirable temperature. When not in use, the handy controller is held in a holder provided on one of the belt portions.

It is further preferable that the warmer of the present invention comprises a time control section for controlling a combustion time in the catalytic burning section. Preferably, the time control section stops the fuel gas supplied to the catalytic burning section in response to an elapse of a predetermined time during a supplying operation of the fuel gas from the fuel tank to the catalytic burning section.

BRIEF DESCRIPTION OF THE DRAWINGS

The above and other objects, features and advantages of the present invention will become more apparent from the following detailed description which is to be read in conjunction with the accompanying drawings, in which:

FIG. 3A is an exploded perspective view showing a detachable assembly of the warmer in accordance with the first embodiment of the present invention;

FIG. 3B is a perspective view showing a belt portion of the warmer in accordance with the first embodiment of the present invention;

FIG. 4 is a cross-sectional view showing an arrangement of the detachable assembly shown in FIG. 3A;

DESCRIPTION OF THE PREFERRED EMBODIMENTS

Figure 1:
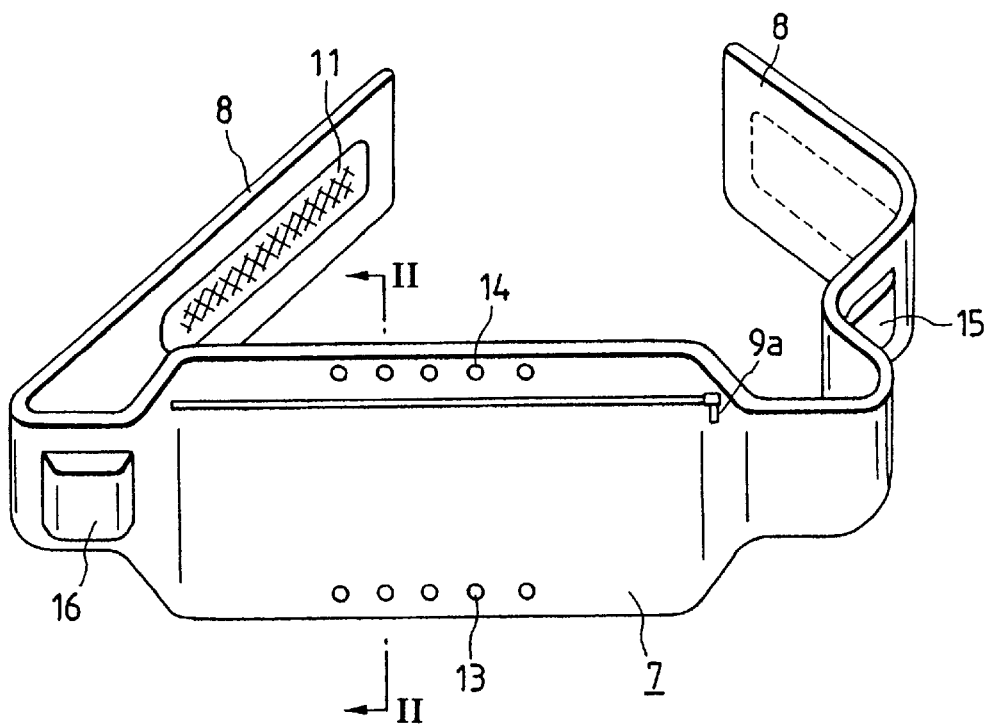
FIG. 1 is a perspective view showing a warmer in accordance with a first embodiment of the present invention.
Figure 2:
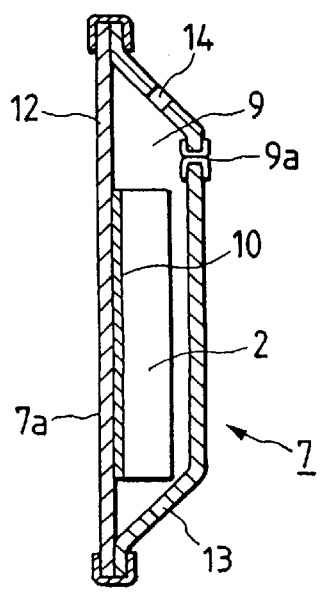
FIG. 2 is a cross-sectional view taken along a line II—II of FIG. 1.

Preferred embodiments of the present invention will be explained in more detail with reference to FIGS. 1 through 8. Identical parts are denoted by the same reference numerals throughout the drawings.

First Embodiment

In FIGS. 1–4 and 8, a fuel tank 1 is a detachable cartridge type for storing fuel gas, such as liquefied petroleum gas (i.e., LPG), that may be butane or propane or mixture of them. The liquefied fuel gas of the fuel tank 1 is gasified by an appropriate gasifying device (not shown). Then, mixture of the gasified fuel gas and air is supplied to a catalytic burning unit 2 via a flexible hose 3. The catalytic burning unit 2 generates heat by causing a catalytic combustion based on an oxidative reaction between the fuel gas and air.

A control unit 4 is connected to the catalytic burning unit 2 via a flexible hose 5. The control unit 4 controls a temperature of the catalytic burning unit 2 by adjusting a fuel gas amount supplied to the catalytic burning unit 2.

A handy controller 6 is connected to the control unit 4 via an extended cord to remote control the control unit 4. The handy controller 6 has a dial or the like to allow a user to set a desirable temperature. According to the set temperature, the fuel gas is supplied and fired to increase the temperature. After the temperature is sufficiently increased, the combustion is stopped to maintain the set temperature.

A heater section 7 is configured into a planar shape having a heat radiation board 7a to be brought into contact with an arbitrary portion of a user's body to warm the abutting body portion. Belt portions 8 are provided at both ends of the heater section 7. The fuel tank 1, the catalytic burning unit 2 and the control unit 4 are accommodated as an assembly in a housing 9. The housing 9 has a fastener 9a for opening or closing an opening 9b laterally extending along an upper portion of the housing 9. The opening 9b, when opened, is wide enough for installing the assembly of the fuel tank 1, the catalytic burning unit 2 and the control unit 4 into the housing 9, or for removing this assembly out of the housing 9.

A face fastener 10 is provided on each of the fuel tank 1, the catalytic burning unit 2 and the control unit 4 for preventing these members from moving or fluctuating in the housing 9. More specifically, by the provision of the face fastener 10, each of the fuel tank 1, the catalytic burning unit 2 and the control unit 4 is securely fixed to an inside surface of the housing 9 that is a reserve side of the heat radiation board 7a of the heater section 7 to be faced to the user's body.

The face fastener 10 can be replaced by any other members having a comparable function. For example, hooks can be used for fixing these members 1, 2 and 4 to an inside wall of the housing 9. A resilient member, such as a rubber, may be also effective to hold them.

Each belt portion 8, formed by a cloth (fabric) or fiber member, is equipped with a connecting (or fastening) member 11 so that an overall length of engaged belt portions 8 is flexibly adjustable according to a user's body size when the belt portions 8 are wound around the user's body. In other words, when the heater section 7 is brought into contact with the waist of the operator's back, the belt portions 8 are long enough to be engaged by the connecting members 11 at the operator's stomach position.

A cushion member 12 is provided on at least an inside face, or on both the inside and outside faces, of each of the heater section 7 and the belt portions 8.

A plurality of ventilation holes 13 and 14 are provided at lower and upper ends of the housing 9 of heater section 7, respectively. It is preferable to locate these ventilation holes 13 and 14 adjacent to the catalytic burning unit 2 at lower and upper ends thereof so as to serve as intake holes for introducing external fresh air and exhaust holes for scavenging the emission gas produced by the combustion.

A controller holder 15 is provided on an outer face of the belt portion 8. The handy controller 6, extended from the control unit 4, is detachably accommodated in this controller holder 15. The controller holder 15 may be a pocket or a face fastener capable of holding the handy controller 6.

A fuel tank storage 16, storing a spare fuel tank, is provided at an appropriate portion on the belt portion 8. Thus, when the fuel tank 1 becomes empty, it can be easily replaced with the spare fuel tank.

The arrangement of the fuel tank 1, the catalytic burning unit 2 and the control unit 4 will be explained in a greater detail hereinafter.

The fuel tank 1 is detachably installed in a fuel tank unit 17. The fuel tank unit 17 comprises a flexible fuel pipe 18 supplying fuel gas from the fuel tank 1 to the catalytic burning unit 2. A valve 19 is provided at an appropriate portion in a fuel supply passage extending from the fuel tank 1 to the catalytic burning unit 2 to open and close the fuel pipe 18. A start switch 20 is also provided in this fuel tank unit 17.

The catalytic burning unit 2 comprises a combustion section 21 to which the fuel gas is supplied from the fuel tank 1 via the fuel pipe 18. A nozzle 22 is provided to inject the fuel gas into the combustion section 21. An air intake section 23 is provided for introducing fresh air that is mixed with the fuel gas. The mixture of the fuel gas and air is fired by ignition electrodes 24. An ignitor 25 produces a spark by causing a discharge between the ignition electrodes 24. A catalyst 26 promotes an oxidative reaction in the mixture of the fuel gas and air. And, an exhaust section 27 emits the exhaust gas from the combustion section 21.

The control unit 4 comprises a control substrate 29 connected to a temperature sensor 28, such as a thermistor, that is provided in the catalytic burning unit 2 for detecting a temperature of the combustion section 21. The handy controller 6, allowing the user to set a desirable temperature of the combustion section 21, is connected via a signal cord to the control substrate 29. An electric power source 30, such as a battery, is also provided in the control unit 4 to activate the control unit 4. The handy controller 6, extendable from the control unit 4 within a predetermined distance, has a switch 31, i.e., the dial or the like, allowing the user to set a desirable temperature.

As described above, the fuel tank unit 17, the catalytic burning unit 2, the control unit 4 are separate units forming a catalytic heat generating apparatus 32 when they are assembled. Although the catalytic heat generating apparatus 32 of this embodiment is formed by a total of three separate units, it is possible to integrate the fuel tank unit 17 and the control unit 4 into a single unit to reduce the number of the separate units from three to two.

Operation of the above-described catalytic heat generating apparatus 32 will be explained hereinafter. When the start switch 20 is turned on, the valve 19 is opened to supply fuel gas from the fuel tank 1 to the combustion section 21 via the fuel pipe 18. The gasified fuel gas is supplied to the combustion section 21. The fuel gas injected from the nozzle 22 is mixed with air supplied from the air intake section 23. The air supplied from the air intake section 23 is introduced from the ventilation holes 13.

In response to the timing-on operation of the start switch 20, the electric power source 30 is turned on in the control unit 4.The ignitor 25 is activated in response to a signal generated from the control unit 4. The ignition electrodes 24 cooperatively cause a spark that ignites the mixture in the combustion section 21. The catalyst 26 promotes the oxidative reaction. Thus, heat is generated by a catalytic combustion based on the oxidative reaction between the fuel gas and air. The exhaust gas, caused by the combustion, is emitted from the combustion section 21 via the exhaust section 27 and other ventilation holes 14 to the outside space.

A user can set the temperature arbitrarily by manipulating the handy controller 6 extended from the control unit 4. The temperature sensor 28 detects a temperature of the combustion section 21. The control unit 4 feedback controls a fuel gas amount supplied to the combustion section 21 so as to maintain the temperature to a set value.

The heater section 7, at its heat radiation board 7a, is brought into contact with an arbitrary portion, such as a waist or a shoulder, of the user's body by winding the belt portions 8 around the user's body and engaging the connecting members 11. The heat generated from the catalytic burning unit 2 is transferred via the heat radiation board 7a of heater section 7 to the user's body. The control unit 4 accurately controls the temperature of the catalytic burning section 2 according to user's preference entered through the handy controller 6. This makes it possible to provide a comfortable and safe warmer responsive to an ambient temperature and user's preference.

As the liquefied fuel gas stored in the fuel tank 1 is a heat source requiring no electric power, this warmer needs not be connected to a commercial electric power source terminal and therefore can be carried to any place the user wants. All of the catalytic burning unit 2, the fuel tank 1 and the controller 4 can be easily taken out of the housing 9. The fuel tank 1 is rechargeable, (i.e., may be refilled) compact in size, and appropriate for long use.

Moreover, each of the catalytic burning unit 2, the fuel tank 1 and the controller 4 is securely held in the housing 9. This arrangement is effective to prevent undesirable dislocation or bump-like motion of the catalytic burning unit 2 or other members in the housing 9 even when the user moves, as when walking or running. Thus, the first embodiment provides a comfortable warmer capable of warming an intended portion of the user's body accurately at a desired temperature.

Figure 8:
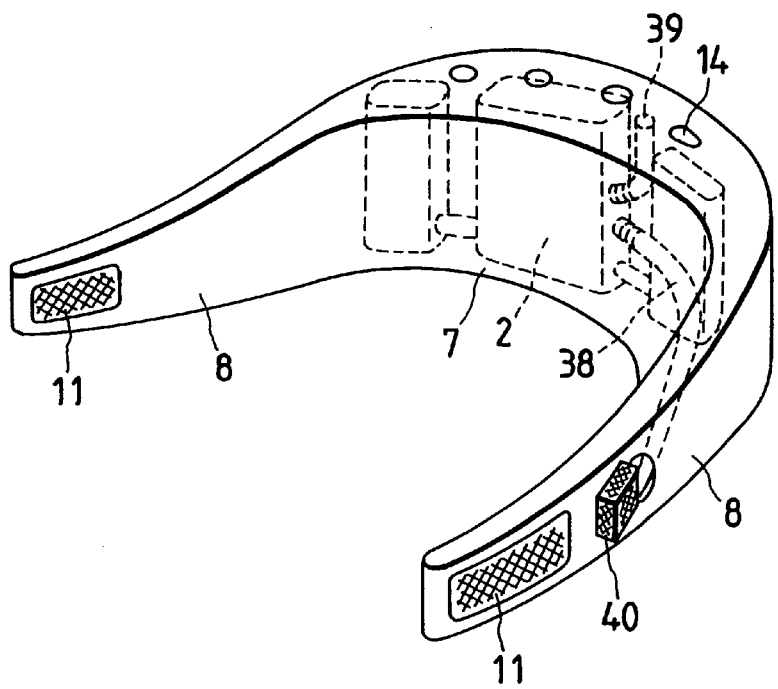
FIG. 8 is a perspective view showing the warmer in accordance with the first embodiment of the present invention.

An intake pipe 38 is provided for introducing fresh air to the air intake section 23 from an external space. An exhaust pipe 39 is connected to the exhaust section 27 for emitting the combustion gas to the external space. As shown in FIG. 8, one end of the intake pipe 38 is connected to the intake section 23, and the other end of the intake pipe 38 is connected to an air filter 40 located in the belt portion 8. Although not shown in the drawing, the exhaust pipe 39 can be arranged in the same manner as the intake pipe 38. According to this pipe arrangement, the ends of intake and exhaust passages (i.e., intake and exhaust ports) can be positioned far from each other. The fresh air is introduced from the external space via a gas permeable outer wall of the belt section 8, the air filter 40, the intake pipe 38 to the intake section 23.

Furthermore, as shown in FIG. 4, the control unit 4 comprises a time control section 41 for controlling a combustion time in the catalytic burning unit 2. The time control section 41 is equipped with a timer (not shown) for measuring an elapse of time during a supplying operation of the fuel gas from the fuel tank 1 to the catalytic burning unit 2. After the predetermined time has passed, the timer control section 41 of the control unit 4 closes the valve 19 to stop the fuel gas supplied to the catalytic burning unit 2.

Second Embodiment

Figure 5:
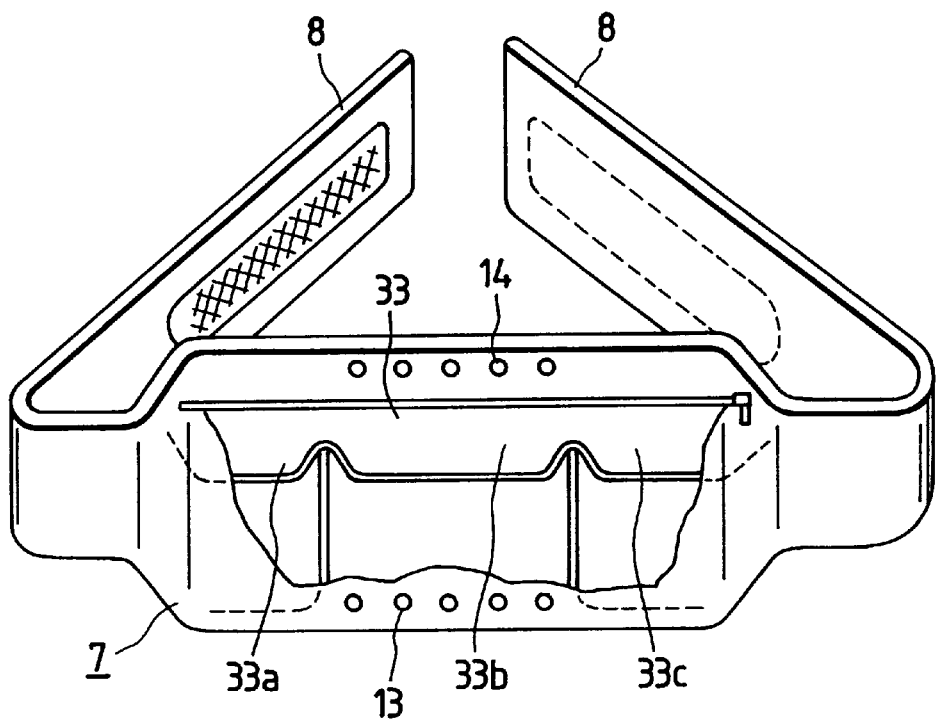
FIG. 5 is a partly broken view showing a warmer in accordance with a second embodiment of the present invention.

As shown in FIG. 5, a second embodiment provides a housing 33 consisting of a plurality of separate housing compartments 33a, 33b and 33c accommodating the fuel tank 1, the catalytic burning unit 2 and the control unit 4, respectively. The catalytic burning unit 2 is accurately positioned at a center when the belt portions 8 are wound around the operator's body and fixed by the connecting members 11. The rest of the arrangement is substantially the same as the components shown in the first embodiment.

According to the arrangement of the second embodiment, the fuel tank 1, the catalytic burning unit 2 and the control unit 4 need not be fixed to the inside wall of the housing 9 since they are accurately positioned in the separate compartments 33a, 33b and 33c without changing their mutual positional relationship. Thus, even when the user moves while walking or running, it is possible to surely prevent undesirable mutual dislocation of these members. Thus, the second embodiment provides a comfortable warmer capable of warming an intended portion of the user's body accurately at a desired temperature.

Third Embodiment

Figure 6:
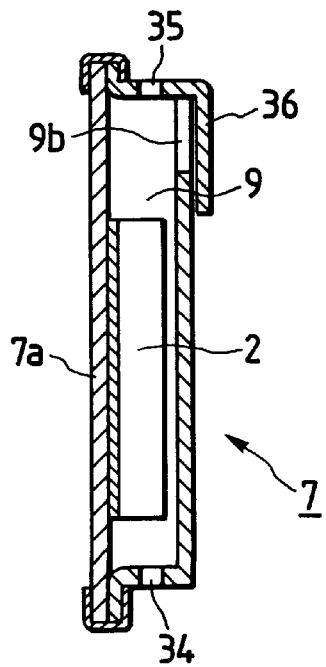
FIG. 6 is a cross-sectional view showing an essential arrangement of a warmer in accordance with a third embodiment of the present invention.

As shown in FIG. 6, a third embodiment provides a plurality of lower ventilation holes 34 on a bottom of the housing 9 (although only one hole 34 is shown in FIG. 6). A plurality of upper ventilation holes 35 are provided on a top of the housing 9 (although only one hole 35 is shown in FIG. 6). More specifically, the upper ventilation holes 35 are opened on a lid 36 closing the housing 9. The rest of the arrangement is substantially the same as the components shown in the first embodiment.

According to the arrangement of the third embodiment, air can be smoothly introduced into the housing 9 via the lower ventilation holes 34 provided at the bottom of the housing 9 without causing any interference with user's clothes. Thus, the catalytic burning unit 2 accommodated in the housing 9 can receive a sufficient amount of fresh air for adequately maintaining the catalytic combustion.

Furthermore, the exhaust gas can be smoothly emitted from the upper ventilation holes 35 provided at the top of the housing 9.

Fourth Embodiment

Figure 7:
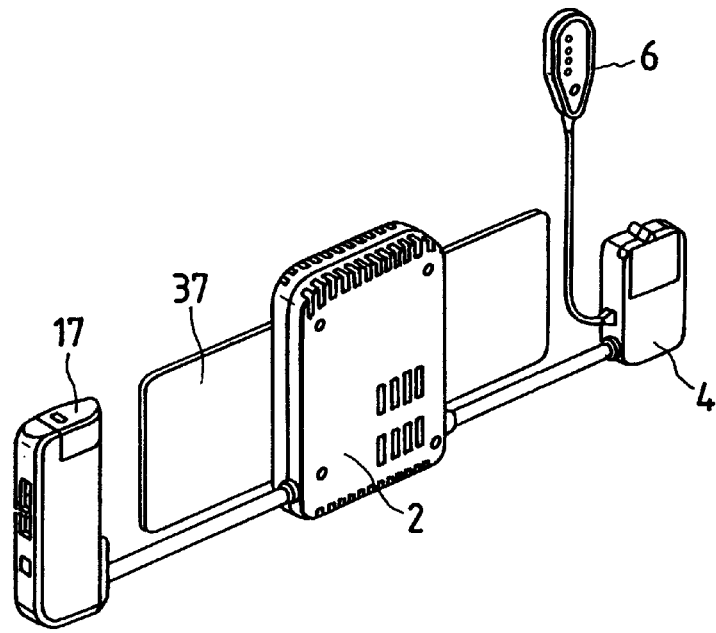
FIG. 7 is a perspective view showing a detachable assembly of a warmer in accordance with a fourth embodiment of the present invention.

As shown in FIG. 7, a fourth embodiment provides a heat transfer board 37 formed by a thin metallic plate which is positioned in the housing 9 of the heater section 7. The heat transfer board 37 extends from the catalytic burning unit 2 toward each belt portion 8. For example, the heat transfer board 37 is made of a heat conductive member, such as aluminum. Furthermore, the heat transfer board 37 may be a flexible member, such as a metallic fabric or a metallic net, that is easily bent along a curve of the user's body. The rest of the arrangement is substantially the same as the components shown in the first embodiment.

According to the arrangement of the fourth embodiment, it becomes possible to smoothly diffuse the heat generated from the catalytic burning unit 2 via the heat transfer board 37 to the heat radiation board 7a of heater section 7 and the belt portion 8. A wide area of the user's body can be warmed up via a curved heat transfer surface along the user's body. Thus, the heat of catalytic burning unit 2 can be effectively transmitted to the user's body.

As described above, according to the embodiments of the present invention, a catalytic burning type warmer comprises a catalytic heat generating apparatus, a heater section, and a pair of belt portions. The catalytic heat generating apparatus comprises a fuel tank for storing fuel gas, and a catalytic burning section connected to the fuel tank for generating heat based on an oxidative reaction between the fuel supplied from the fuel tank and air. The heater section comprises a housing for accommodating the catalytic heat generating apparatus. The belt portions are provided at both ends of the heater section for fixing the heater section to a user's body. With this arrangement, it becomes possible to warm a desirable portion of the user's body safely and properly at any place without connecting the warmer to a commercial power source.

Furthermore, the housing has an opening for taking the catalytic heat generating apparatus into and out of the housing. This arrangement makes it possible to take the catalytic burning section, the fuel tank and the control section out of the housing. Repair and adjustment of each component can be easily done. The heater section, which may be subjected to sweat, can be washed and kept clean.

Furthermore, the catalytic burning section is securely held in the housing by an appropriate fixing member. This arrangement makes it possible to prevent the catalytic burning section or the like from dislocating or fluctuating in the housing even when the user moves for walking or running, providing a stabilized heating performance.

Furthermore, the catalytic heat generating apparatus comprises a plurality of separate units, and the fuel tank is connected to the catalytic burning section via a flexible connecting member. This provides a good weight balance in installing the heat generating components into the heater section. This gives a better feeling to the user when the warmer is used, without causing an undesirable leaning of the apparatus components.

Furthermore, the heater section comprises a plurality of ventilation holes for communicating an inside space of the housing with an external space. With this arrangement, external air can be smoothly introduced into the catalytic burning section. The exhaust gas produced by the combustion in the catalytic burning section can be smoothly emitted.

Furthermore, at least part of the ventilation holes is provided on a bottom of the housing. This arrangement prevents the holes from being closed by a jacket or a coat when the user wears it on the warmer.

Furthermore, the catalytic burning section comprises an intake section for introducing air from an external space and an exhaust section for emitting combustion gas. At least one passage is provided to connect either of the intake and exhaust sections to the external space. Preferably, the passage has one end connected to either of the intake and exhaust sections and the other end extended to one of the belt portions and communicated with the external space. With these arrangement, the intake and exhaust passages can be separated far enough for maintaining the catalytic combustion adequately.

Furthermore, the heater section comprises a heat transfer board for diffusing the heat generated effectively from the catalytic burning section. With this arrangement, the heat generated from the catalytic burning section can be smoothly transferred from the heater section to the belt portion. This makes it possible to warm a wide area of the user's body.

Furthermore, a cushion member is provided on at least one of the heater section and the belt portions. It becomes possible to fit the warmer along the user's body with an adequate resilient force. A movement of the user can be absorbed, and a preferable feeling can be obtained when the warmer is used.

Furthermore, the fuel tank is detachable from the catalytic heat generating apparatus, and a storage is provided on at least one of the belt sections for storing a spare fuel tank. With this arrangement, it becomes easy to carry the spare fuel tank. This is advantageous to downsize each fuel tank and reduce the weight. It becomes possible to warm the user's body for a relatively long time by exchanging the fuel tanks.

Furthermore, a control section is provided for feedback controlling a temperature of the catalytic burning section to a set value. With this arrangement, it becomes possible to warm a desirable portion of the user's body safely and properly at any place in accordance with an ambient temperature or user's preference.

Furthermore, the control section is associated with a handy controller for allowing a user to set a desirable temperature. The handy controller may be detachably held in a holder provided on one of the belt portions. With these arrangement, the user can easily control the set temperature and perform the on-and-off operation while the user wears the warmer. This provides an improved facilitation for the warmer.

Preferably, a time control section is provided in the control section for controlling a combustion time in the catalytic burning section. The time control section stops the fuel gas supplied to the catalytic burning section in response to an elapse of a predetermined time after starting a supplying operation of the fuel gas from the fuel tank to the catalytic burning section.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A warmer comprising:
   a catalytic heat generating apparatus comprising a fuel tank for storing liquefied combustible gas, and a catalytic burning section connected to said fuel tank for generating heat of catalytic combustion based on an oxidative reaction of said combustible gas supplied from said fuel tank and air;
   a heater section comprising a housing for accommodating said catalytic heat generating apparatus; and
   a pair of belt portions provided at both ends of said heater section for fixing said heater section to a user's body,
   wherein said catalytic heat generating apparatus comprises a plurality of housing units including a housing unit of said fuel tank and a housing unit of said catalytic burning section which are connected via a flexible connecting member.

2. The warmer in accordance with claim 1, wherein said housing has an opening for taking said catalytic heat generating apparatus into and out of said housing.

3. The warmer in accordance with claim 1, wherein said catalytic burning section is securely held in said housing by a fixing member.

4. The warmer in accordance with claim 1, wherein said heater section comprises a plurality of ventilation holes for communicating an inside space of said housing with an external space.

5. The warmer in accordance with claim 4, wherein at least part of said ventilation holes is provided on a bottom of said housing.

6. The warmer in accordance with claim 1, wherein said catalytic burning section comprises an intake section for introducing air from an external space and an exhaust section for emitting combustion gas, and at least one passage is provided to connect either of said intake and exhaust sections to the external space.

7. The warmer in accordance with claim 1, wherein said heater section comprises a heat transfer board for diffusing the heat generated from said catalytic burning section.

8. The warmer in accordance with claim 1, wherein a cushion member is provided on at least one of said heater section and said belt portions.

9. The warmer in accordance with claim 1, wherein
   said plurality of separate housing units comprise a first housing unit and a second housing unit,
   said first housing unit accommodates said catalytic burning section, and
   said second housing unit accommodates a control section for controlling combustion of said catalytic burning section.

10. A warmer as recited in claim 1, wherein said catalytic heat generating apparatus is detachable from said housing of said heater section for easing maintenance of said catalytic heat generating apparatus as well as cleaning of said heater section.

11. A warmer comprising:
    a catalytic heat generating apparatus, comprising a fuel tank for storing liquefied combustible gas, and a catalytic burning section connected to said fuel tank for generating heat of catalytic combustion based on an oxidative reaction of said combustible gas supplied from said fuel tank and air;
    a heater section comprising a housing for accommodating said catalytic heat generating apparatus; and
    a pair of belt portions provided at both ends of said heater section for fixing said heater section to a user's body,
    wherein said catalytic burning section comprises an intake section for introducing air from an external space and an exhaust section for emitting combustion gas, and at least one passage is provided to connect either of said intake and exhaust sections to the external space, and
    said passage has one end connected to said either of said intake and exhaust sections and the other end extended to one of said belt portions and communicated with said external space.

12. A warmer as recited in claim 11, wherein said catalytic heat generating apparatus is detachable from said housing of said heater section for easing maintenance of said catalytic heat generating apparatus as well as cleaning of said heater section.

13. A warmer comprising:
    a catalytic heat generating apparatus, comprising a fuel tank for storing liquefied combustible gas, and a catalytic burning section connected to said fuel tank for generating heat of catalytic combustion based on an oxidative reaction of said combustible gas supplied from said fuel tank and air;
    a heater section comprising a housing for accommodating said catalytic heat generating apparatus; and
    a pair of belt portions provided at both ends of said heater section for fixing said heater section to a user's body,
    wherein said fuel tank is detachable from said catalytic heat generating apparatus, and a storage is provided on at least one of said belt sections for storing a spare fuel tank.

14. A warmer as recited in claim 13, wherein said catalytic heat generating apparatus is detachable from said housing of said heater section for easing maintenance of said catalytic heat generating apparatus as well as cleaning of said heater section.

15. A warmer comprising:

a catalytic heat generating apparatus comprising a fuel tank for storing liquefied combustible gas, a catalytic burning section connected to said fuel tank for generating heat of catalytic combustion based on an oxidative reaction of said combustible gas supplied from said fuel tank and air, and a time control section for feedback controlling a temperature of said catalytic burning section to a set value;

a heater section comprising a housing for accommodating said catalytic heat generating apparatus; and a pair of belt portions provided at both ends of said heater section for fixing said heater section to a user's body.

16. The warmer in accordance with claim 15, wherein said control section is associated with a hand operated controller for allowing a user to set a desirable temperature.

17. The warmer in accordance with claim 16, wherein said hand operated controller is held in a holder provided on one of said belt portions.

18. A warmer as recited in claim 15, wherein said catalytic heat generating apparatus is detachable from said housing of said heater section for easing maintenance of said catalytic heat generating apparatus as well as cleaning of said heater section.

19. A warmer comprising:

a catalytic heat generating apparatus comprising a fuel tank for storing liquefied combustible gas, a catalytic burning section connected to said fuel tank for generating heat of catalytic combustion based on an oxidative reaction of said combustible gas supplied from said fuel tank and air, and a time control section for controlling a combustion time in said catalytic burning section;

a heater section comprising a housing for accommodating said catalytic heat generating apparatus; and a pair of belt portions provided at both ends of said heater section for fixing said heater section to a user's body.

20. The warmer in accordance with claim 19, wherein said time control section stops supply of said combustible gas to said catalytic burning section in response to an elapse of a predetermined time during a supplying operation of said combustible gas from said fuel tank to said catalytic burning section.

21. A warmer comprising:

a catalytic heat generating apparatus comprising a fuel tank for storing liquefied combustible gas, a catalytic burning section connected to said fuel tank for generating heat of catalytic combustion based on an oxidative reaction of said combustible gas supplied from said fuel tank and air, and a temperature control section for feedback controlling a temperature of said catalytic burning section to a set value;

a heater section comprising a housing for accommodating said catalytic heat generating apparatus, said housing having an opening for taking said catalytic heat generating apparatus into and out of said housing; and a pair of belt portions provided at both ends of said heater section for fixing said heater section to a user's body.

22. A warmer comprising:

a catalytic heat generating apparatus comprising a fuel tank for storing liquefied combustible gas, a catalytic burning section connected to said fuel tank for generating heat of catalytic combustion based on an oxidative reaction of said combustible gas supplied from said fuel tank and air, and a time control section for controlling a combustion time in said catalytic burning section;

a heater section comprising a housing for accommodating said catalytic heat generating apparatus, said housing having an opening for taking said catalytic heat generating apparatus into and out of said housing; and a pair of belt portions provided at both ends of said heater section for fixing said heater section to a user's body.

\* \* \* \* \*